United States Patent
Wurtman

(10) Patent No.: US 8,691,775 B2
(45) Date of Patent: Apr. 8, 2014

(54) USE OF DRUGS THAT ACTIVATE P2Y RECEPTORS TO ENHANCE SYNAPTOGENESIS

(75) Inventor: Richard Wurtman, Boston, MA (US)

(73) Assignee: Back Bay Scientific, LLC, Boston, MA (US)

( * ) Notice: Subject to any disclaimer, the term of this patent is extended or adjusted under 35 U.S.C. 154(b) by 0 days.

(21) Appl. No.: 13/090,122

(22) Filed: Apr. 19, 2011

(65) Prior Publication Data

US 2011/0257109 A1    Oct. 20, 2011

Related U.S. Application Data

(60) Provisional application No. 61/325,569, filed on Apr. 19, 2010.

(51) Int. Cl.
*A61K 31/7076* (2006.01)

(52) U.S. Cl.
USPC .......................................................... 514/25

(58) Field of Classification Search
USPC .......................................................... 514/25
See application file for complete search history.

(56) References Cited

U.S. PATENT DOCUMENTS

| | | | |
|---|---|---|---|
| 5,470,838 A | 11/1995 | von Borstel et al. | |
| 5,583,117 A | 12/1996 | von Borstel et al. | |
| 6,864,243 B1 * | 3/2005 | Peterson | 514/47 |
| 2005/0187182 A1 * | 8/2005 | Wurtman et al. | 514/49 |
| 2006/0241077 A1 | 10/2006 | Wurtman et al. | |
| 2007/0004670 A1 | 1/2007 | Wurtman et al. | |
| 2009/0029909 A1 | 1/2009 | Barres et al. | |
| 2010/0022567 A1 | 1/2010 | Wurtman et al. | |
| 2010/0041621 A1 | 2/2010 | Renshaw et al. | |

OTHER PUBLICATIONS

Antonova et al. The relationship between brain structure and neurocognition in schizophrenia: a selective review. Schizophr Res 70:117-145, Feb. 2004.*
Wurtman RJ. Synapse formation and cognitive brain development: effect of docosahexaenoic acid and other dietary constituents. Metabol Clin Exp 57(Suppl 2):S6-S10, 2008.*
Jacobson et al., "Development of selective agonists and antagonists of P2Y Receptors," Purinergic Signalling (2009) 5:75-89.
Kim et al., "Methanocarba Modification of Uracil and Adenine Nucleotides: High Potency of Northern Ring Conformation at P2Y1, P2Y2, P2Y4, and P2Y11 but Not P2Y6 Receptors," J. Med. Chem., 2002, 45 (1), pp. 208-218.
International Search Report and Written Opinion of corresponding International Application No. PCT/US11/33097 dated Jul. 1, 2011.

* cited by examiner

*Primary Examiner* — Wu-Cheng Winston Shen
*Assistant Examiner* — Yih-Horng Shiao
(74) *Attorney, Agent, or Firm* — Mark S. Cohen; Pearl Cohen Zedek Latzer Baratz LLP

(57) ABSTRACT

The present invention encompasses compositions and methods that activate P2Y receptors for the increased production of new synapses in the central nervous system. The formulations of the invention may be administered to a healthy subject or to a subject in need thereof to restore synapses.

12 Claims, No Drawings

USE OF DRUGS THAT ACTIVATE P2Y RECEPTORS TO ENHANCE SYNAPTOGENESIS

CROSS REFERENCE TO RELATED APPLICATIONS

This application claims priority to U.S. Provisional Application No. 61/325,569, filed on Apr. 19, 2010, hereby incorporated by reference.

FIELD OF THE INVENTION

The present invention encompasses compositions of active agents and phosphatide precursors, which increase the production of new synapses in the central nervous system and to methods of use of the compositions to increase cognitive function or treat diseases associated synapse deficiency The compositions of the invention may be administered to a healthy subject or to a subject in need of synaptic restoration after loss due to a disease or injury or to a healthy subject desiring to improve cognition.

BACKGROUND OF THE INVENTION

Deficiencies in particular groups of synapses are responsible, entirely or in part, for the progressive development of many neurologic and/or behavioral diseases. These diseases include, but are not limited to, neurogenerative diseases, such as Alzheimer's disease, Parkinson's Disease, Huntington's Disease, Prion Disease, and Amyotrophic lateral sclerosis; toxic neuropathies; meningoencephalopathies; vascular diseases, such as loss of brain mass resulting from a stroke; and genetic disorders. Other factors may cause deficiencies in groups of synapses, such as injuries including traumatic injuries to the brain or spinal cord and malnutrition. Despite research progress, there is no real cure that prevents, delays, stops, or reverses the nerve cell damage that leads to the devastating symptoms of most of these diseases and most therapies focus on controlling the symptoms. Accordingly, there is an urgent need in the art to develop drug compositions that enhance synaptogenesis for prophylactic and therapeutic use.

SUMMARY OF THE INVENTION

It is therefore an object of the invention to provide solutions to the aforementioned deficiencies in the art.

In one embodiment the invention encompasses compositions comprising at least one active agent that activates P2Y receptors in an amount sufficient to improve cognitive or neurological function in a subject. In another embodiment the composition further comprises at least one phosphatide precursor. The active agent may be ADP, 2-methylthio-ADP trisodium salt, ATP, ATP disodium salt, α,β-methylene ATP, α,β-methyleneadenosine 5'-triphosphate trisodium salt, 2-methylthioadenosine triphosphate tetrasodium salt, 2-MeSATP, BzATP triethylammonium salt, cytidine, acylated cytidines, cytidine-monophosphate (CMP), cytidine-diphosphate (CDP), cytidine-triphosphate (CTP), CDP-choline, CMP-choline, denufosol, denufosol tetrasodium, GTP, ITP, MRS 2341, MRS 2365, MRS 2690, MRS 2698, PSB 0474, uridine 5'-diphosphate (UDP), UDP-glucose, uridine β-thiodiphosphate (UDPβS), uridine 5'-triphosphate (UTP), uridine γ-thiophosphate (UTPγS), 2-thioUTP tetrasodium salt, UTPγS trisodium salt, uridine-5'-diphosphoglucose, diuridine triphosphate, 2-(hexylthio) (HT)-AMP, diadenosine pentaphosphate, 2'-deoxy-2'-amino-UTP, 2-thio-UTP, triacetyluridine, diacetyl/acyl uridine, suramin, dipyridamole analogs, diadenosine tetraphosphate $Ap_4U$, $Ap_4A$, INS365, INS37217, or INS48823. The phosphatide precursor may be uridine, a uridine precursor, an omega-3 fatty acid, glucose, or choline, and preferably it is uridine, uridine-monophosphate, DHA, EPA, glucose, or choline. The active agent may be present in an amount between about 0.1 mg and 500 mg, and preferably it is present in an amount between about 0.5 mg and 100 mg.

In one embodiment of the invention, the composition may be administered orally, nasally, parenterally, systemically, intraperitoneally, or topically.

Another embodiment of the invention encompasses a method for improving cognitive or neurological function in a subject comprising administering a therapeutically effective amount of at least one active agent that activates P2Y receptors to a subject in need of such therapy. In another embodiment, the method further comprises administering at least one phosphatide precursor to the subject.

In one embodiment, the improvement in cognitive function is measured as a score increase between about 1% and 20% in the in the delayed verbal recall task of the Wechsler Memory Scale-revised, and preferably, the improvement in cognitive function is measured as a score increase between about 1% and 10% in the in the delayed verbal recall task of the Wechsler Memory Scale-revised. In another embodiment of the invention, the improvement in cognitive function is measured as a score increase between about 1% and 5% in the in the delayed verbal recall task of the Wechsler Memory Scale-revised.

In one embodiment of the method, the active agent is ADP, 2-methylthio-ADP trisodium salt, ATP, ATP disodium salt, α,β-methylene ATP, α,β-methyleneadenosine 5'-triphosphate trisodium salt, 2-methylthioadenosine triphosphate tetrasodium salt, 2-MeSATP, BzATP triethylammonium salt, cytidine, acylated cytidines, cytidine-monophosphate (CMP), cytidine-diphosphate (CDP), cytidine-triphosphate (CTP), CDP-choline, CMP-choline, denufosol, denufosol tetrasodium, GTP, ITP, MRS 2341, MRS 2365, MRS 2690, MRS 2698, PSB 0474, uridine 5'-diphosphate (UDP), UDP-glucose, uridine β-thiodiphosphate (UDPβS), uridine 5'-triphosphate (UTP), uridine γ-thiophosphate (UTPγS), 2-thioUTP tetrasodium salt, UTPγS trisodium salt, uridine-5'-diphosphoglucose, diuridine triphosphate, 2-(hexylthio) (HT)-AMP, diadenosine pentaphosphate, 2'-deoxy-2'-amino-UTP, 2-thio-UTP, triacetyluridine, diacetyl/acyl uridine, suramin, dipyridamole analogs, diadenosine tetraphosphate $Ap_4U$, $Ap_4A$, INS365, INS37217, or INS48823. The phosphatide precursor may be uridine, a uridine precursor, an omega-3 fatty acid, glucose, or choline and preferably, the phosphatide precursor is uridine, uridine-monophosphate, DHA, EPA, glucose, or choline. In one embodiment of the invention, the active agent is present in an amount between about 0.1 mg and 500 mg, and preferably, the active agent is present in an amount between about 0.5 mg and 100 mg.

In one embodiment of the invention, the subject suffers from a neurogenerative disease selected from the group consisting of Alzheimer's disease, Parkinson's Disease, Huntington's Disease, Prion Disease, and Amyotrophic lateral sclerosis. In another embodiment, the subject has suffered a concussion, a stroke, partial or total spinal cord transection, brain injury, or malnutrition. In yet another embodiment, the subject has suffered toxic neuropathies, meningoencephalopathies, or a vascular disease.

Yet another embodiment of the invention encompasses a method for increasing the level of synaptic proteins in a subject comprising administering a composition having at least one active agent, wherein the synaptic proteins is NF-70, NF-M, PSD-95, or mGluR. In another embodiment, the composition further comprises at least one phosphatide precursor.

Another embodiment of the invention provides an in vitro method for screening a drug for enhancing brain synaptogenesis and/or activating brain P2Y receptors, comprising incubating neuron-derived cells with the drug, and determining the effect of the drug on the level of synaptic proteins and neurites in the cells. In another embodiment, the incubation step of the in vitro method further comprises adding phosphatide precursors including uridine, DHA or EPA, glucose, and choline to the drug.

In yet a further embodiment, the invention provides an ex vivo method for screening a drug for enhancing brain synaptogenesis and/or activating brain P2Y receptors, comprising feeding an animal with a synthetic diet comprising the drug and determining the effect of the drug on the number of dendritic spines and synaptic protein activity in brain samples isolated from the animal. In another embodiment, the ex vivo method further comprises feeding the animal at least one phosphatide precursors including uridine, DHA or EPA, glucose, and choline.

DETAILED DESCRIPTION OF THE PRESENT INVENTION

Synapses are functional connections between neurons or between neurons and other types of cells. Dendritic spines are small protrusions that cover most neurons in the brain. Synapses are essential to neuronal function and their loss is linked to the progressive development of many neurologic and/or behavioral diseases as well as to injury. The current invention encompasses compositions and methods for treating a subject in need of treatment of a disorder linked to synapse deficiency. These deficiencies may be either causal or symptomatic of a disorder that includes, among others, aging, neurogenerative diseases, traumatic injuries to the brain or spinal cord, and vascular diseases.

Not to be limited by theory, it is believed that synthetic agonists (active agents) with high affinity for or potency at P2Y receptors are much more potent than uridine alone in promoting synaptogenesis. In turn, an increase in the rate of synaptogenesis enhances cognition and the release of some neurotransmitters. Accordingly, the present invention encompasses methods of improving cognition by enhancing synaptogenesis comprising administering at least one active agent that activates P2Y receptors to a subject in need of such therapy. The present invention also encompasses compositions comprising at least one active agent that activates P2Y receptors and at least one phosphatide precursor. The invention also encompasses methods of improving cognitive or neurological function by administering a therapeutically effective amount of either composition to a subject in need of such therapy or a subject desiring to increase cognitive or neurological function. Further, the invention encompasses methods of treating diseases associated with synapse deficiency by administering at least one active agent that activates P2Y receptors to a subject in need of such therapy. The invention also encompasses methods of treating diseases wherein the subject also is administered at least one phosphatide precursor.

As used herein, the term "synapse deficiency" refers to the loss of existing synapses or a decreased production of new synapses in the central nervous system. The decrease in synapses may be due to (a) a decrease in the number of neurons that make the synapses; (b) a decrease in the average number of synapses that each of the relevant neurons make; or (c) both. Synapse deficiency is implicated in a variety of pathological and degenerative processes that include, among others, neurogenerative diseases, such as Alzheimer's disease, Parkinson's Disease, Huntington's Disease, Prion Disease and Amyotrophic lateral sclerosis; traumatic injuries to the brain (such as concussion, blast injury, combat-related injury) or spinal cord (such as partial or total spinal cord transection); malnutrition; toxic neuropathies; meningoencephalopathies; vascular diseases, such as loss of brain mass resulting from a stroke; genetic disorders; and aging.

As used herein, the term "subject" refers to an animal. Preferably, the animal is a mammal, including a human and non-human mammal. The subject may be a healthy subject or a subject suffering from synapse deficiency.

As used herein, when the term "between" is used to describe a range, the term is meant to include the entire scope of the range as well as the endpoints, unless otherwise noted.

As used herein, the term "patient" refers to a subject in need of treatment of a disorder linked to synapse deficiency. Further, as used herein, the terms "disease," "condition" and "disorder" may all be used interchangeably.

As used herein, the term "active agent" refers to a compound that activates P2Y receptors to increase production of new synapses in the central nervous system.

As used herein, the term "pharmaceutically effective amount" refers to an amount effective to elicit a cellular response that is clinically significant. A clinically significant amount is an amount that is greater than the baseline established using a cognitive test, such as the delayed verbal recall task of the Wechsler Memory Scale-revised.

The compositions and methods encompassed by the invention may be used to treat subjects with a pre-existing disorder linked to synapse deficiency, or to treat subjects pre-disposed to a disorder linked to synapse deficiency. Additionally, the compositions and methods of the invention may be used to correct cellular or physiological abnormalities in the central nervous system of a subject with a pre-existing disorder linked to synapse deficiency or with a pre-disposed condition to a disorder linked to synapse deficiency in the central nervous system. Furthermore, the compositions and methods of the invention may be used to increase neuron survival and neuron synaptic connections in subjects with a pre-existing disorder linked to synapse deficiency or with a pre-disposed condition to a disorder linked to synapse deficiency in the central nervous system, as well as in subjects receiving neurotransplantation. Also, the compositions and methods encompassed by the invention may be used to treat subjects desiring to improve cognitive function.

As described above, the present invention encompasses compositions and methods of activating P2Y receptors in the brain or central nervous system as a way to prevent or treat synapse deficiency and improve cognitive or neurological function. The compositions of the invention comprise at least one active agent that activates P2Y receptors in an amount sufficient to improve cognitive or neurological function in a subject. The composition may further comprise at least one phosphatide precursor.

P2Y receptors are a family of purinergic receptors and G protein-coupled receptors and are present in almost all human tissues where they exert various biological functions based on their G-protein coupling. P2Y receptors are G-protein-coupled receptors and different subtypes of these receptors are involved in a wide variety of processes, including platelet aggregation, vasodilation, neuromodulation, ion flux, differentiation and synaptic communication. Recognized members of the P2Y receptor family are the mammalian $P2Y_1$, $P2Y_{11}$, P2Y$_{12}$ and P2Y$_{13}$ receptors, which respond to adenine nucleotides; the P2Y$_4$, P2Y$_6$ and P2Y$_{14}$ receptors, that respond to uracil nucleotides; and the P2Y$_2$ and rodent P2Y$_4$ receptors, which are of mixed selectivity.

Active agents are compounds that stimulate P2Y receptors, increase their activity, and/or activate protein synthesis and normal neuronal differentiation. Active agents include, but are not limited to, ADP, 2-methylthio-ADP trisodium salt, ATP, ATP disodium salt, α,β-methylene ATP, α,β-methylene-adenosine 5'-triphosphate trisodium salt, 2-methylthioadenosine triphosphate tetrasodium salt, 2-MeSATP, BzATP triethylammonium salt, cytidine, acylated cytidines, cytidine-monophosphate (CMP), cytidine-diphosphate (CDP), cytidine-triphosphate (CTP), CDP-choline, CMP-choline, denufosol, denufosol tetrasodium, GTP, ITP, MRS 2341, MRS 2365, MRS 2690, MRS 2698, PSB 0474, uridine 5'-diphosphate (UDP), UDP-glucose, uridine β-thiodiphosphate (UDPβS), uridine 5'-triphosphate (UTP), uridine γ-thiophosphate (UTPγS), 2-thioUTP tetrasodium salt, UTPγS trisodium salt, uridine-5'-diphosphoglucose, diuridine triphosphate, 2-(hexylthio) (HT)-AMP, diadenosine pentaphosphate, 2'-deoxy-2'-amino-UTP, 2-thio-UTP, triacetyluridine, diacetyl/acyl uridine, suramin, dipyridamole analogs, diadenosine tetraphosphate Ap$_4$U, Ap$_4$A, INS365, INS37217, or INS48823. Acylated uridines (such as diacetyl/acyl uridine) and acylated cytidines are known in the art and can be found in U.S. Pat. Nos. 5,583,117, and 5,470,838, hereby incorporated by reference. Some active agents such as MRS 2365 (CAS No. 436847-09-5), MRS 2690, and PSB 0474 (CAS No. 917567-60-3) are commercially available from Tocris Bioscience (Ellisville, Mo. 63021). Other active agents can be found in the scientific literature such as Ap$_4$U, Ap$_4$A, INS365, INS37217, INS48823, and MRS2698 (see Jacobson et al., "Development of selective agonists and antagonists of P2Y Receptors," Purinergic Signalling (2009) 5:75-89), and MRS 2341 (see Jacobson et al, *J. Med. Chem.*, 2002, 454(1) pp. 208-218), both hereby incorporated by reference.

The amount of active agent should be present in a therapeutically effective amount. A therapeutically effective amount or dose refers to that amount of the active agent sufficient to result in improvement in cognitive or neurological function. Toxicity and therapeutic efficacy of compositions of active agents can be determined by standard pharmaceutical procedures in cell cultures or experimental animals, e.g., for determining the LD$_{50}$ (the dose lethal to 50% of the population) and the ED50 (the dose therapeutically effective in 50% of the population). The dose ratio between toxic and therapeutic effects is the therapeutic index and it can be expressed as the ratio LD$_{50}$/ED$_{50}$. Compositions which exhibit large therapeutic indices are preferred. Data obtained from cell culture assays and animal studies can be used in formulating a range of dosage for use in humans. The dosage of such compositions lies preferably within a range of circulating concentrations that include the ED50 with little or no toxicity. The dosage may vary within this range depending upon the dosage form employed and the route of administration utilized.

Typically, the active agent is present in an amount between about 0.1 mg and 500 mg. Preferably, the active agent is present in an amount between about 0.5 mg and 100 mg. More preferably, the active agent is present in an amount between about 1 mg and 10 mg.

Phosphatide precursors are compounds that cells in the body, in particular neurons, use to increase the quantity of phosphatides, synaptic proteins, neurite outgrowth, and/or the formation of dendritic spines. For example, relatively small increases in the available levels of phosphatide precursors accelerate the production of UTP, CTP, diacylglycerol molecules containing DHA, phosphocholine, and other molecules (intermediates) used in phosphatide synthesis and synaptogenesis. In another example, phosphatide precursors increase the production of phospholipids such as phosphatidylcholine (PC), phosphatidylethanolamine (PE), phosphatidylserine (PS), and/or phosphatidylinositol (PI). Typical phosphatide precursors include, but are not limited to, at least one of uridine, uridine precursors, omega-3 fatty acids, glucose, or choline. As used herein, the term "glucose" encompasses dextrose, D-glucose, or corn syrup. Preferably, phosphatide precursors include at least one of uridine, uridine-monophosphate, DHA, EPA, glucose, or choline. More preferably, phosphatide precursors include uridine, DHA and choline or uridine, EPA, and choline.

As used herein, the term "uridine" includes, but is not limited to, at least one uridine salt or uridine precursor. Uridine salts include, but are not limited to, uridine-5'-monophosphate (UMP), uridine-5'-diphosphate (UDP), uridine-5'-triphosphate (UTP), UDP glucose, or a salt of UMP, UDP, or UTP. Uridine precursors include cytidine-5'-monophosphate, cytidine-5'-diphosphate (CDP), or CDP-glucose. Preferably, uridine includes uridine-5'-monophosphate (UMP), uridine-5'-diphosphate (UDP), uridine-5'-triphosphate (UTP), or a salt of UMP, UDP, or UTP.

Omega-3 fatty acids include, but are not limited to, α-linolenic acid (ALA), stearidonic acid (SDA), eicosatrienoic acid (ETE), eicosatetraenoic acid (ETA), eicosapentaenoic acid (EPA), eicosahexaenoic acid, docosapentaenoic acid (DPA), docosahexaenoic acid (DHA), tetracosapentaenoic acid, tetracosahexaenoic acid, or stearidonic acid. Preferably, the omega-3 fatty acids include DHA or EPA.

As used herein, the term "choline" includes the salt of the quaternary saturated amine of the chemical formula $(CH_3)_3N^+CH_2CH_2OHX^-$, wherein $X^-$ is a negatively charged counterion or a compound that dissociates into choline. Choline salts include, but are not limited to, choline chloride, choline tartrate, choline bitartrate, choline sulfonate, choline citrate, iron-choline citrate complex, or choline stearate. Compounds that dissociate into choline include, but are not limited to, sphingomyelin, cytidine-diphosphocholine (CDP-choline), citicoline, acylglycerophosphocholine, lecithin, lysolecithin, or glycerophosphatidylcholine. Preferably, choline includes choline chloride, choline tartrate, choline bitartrate, choline sulfonate, choline citrate, iron-choline citrate complex, or choline stearate.

The liver is probably the major organ modulating plasma uridine. In rats, for example, more than 90% of the uridine that enters the liver via the portal vein is metabolized in a single pass. Accordingly, the pharmaceutical compositions of the invention may further comprise at least one additional compound that prevents the hepatic degradation of uridine, a uridine degradation inhibitor. In other words, the uridine degradation inhibitor is a compound that is a uridine phosphorylase inhibitor, increases uridine availability, and/or is a uridine renal transport competitor. Uridine phosphorylase inhibitors include, but are not limited to, benzyl barbiturate or derivatives thereof. Uridine renal transport competitors include, but are not limited to, L-uridine, L-2', 3'-dideoxyuridine, or D-2', 3'-dideoxyuridine.

The invention also encompasses methods of improving cognitive or neurological function by administering a therapeutically effective amount of at least one active agent that activates P2Y receptors to a subject in need thereof. In another embodiment, the method may further comprise administering at least one phosphatide precursor with the active agent. Administration of the phosphatide precursor may be simultaneously or sequentially with the active agent. A pharmaceutically effective amount of the composition is an amount effective to elicit a cellular response that is clinically significant. Also, the invention encompasses methods of treating diseases and conditions associated with synapse deficiency including, but not limited to, a variety of pathological and degenerative processes that include, neurogenerative diseases, such as Alzheimer's disease, Parkinson's Disease, Huntington's Disease, Prion Disease, and Amyotrophic lateral sclerosis; traumatic injuries to the brain (such as concussion, blast injury, combat-related injury) or spinal cord (such as partial or total spinal cord transection); malnutrition; toxic neuropathies; meningoencephalopathies; vascular diseases, such as loss of brain mass resulting from a stroke; genetic disorders; and aging.

For example, the invention also encompasses methods of treating Alzheimer's disease by administering a therapeutically effective amount of at least one active agent that activates P2Y receptors to a subject in need thereof, wherein the improvement in cognitive function is measured as an score increase of between about 1% and 20% in the in the delayed verbal recall task of the Wechsler Memory Scale-revised. The method for treating Alzheimer's disease may further comprise administering at least one phosphatide precursor to the subject.

Typically, a clinically significant amount is established by comparing the subject's cognitive function for at least two measurements; however, multiple measurements are equally plausible and also contemplated within the invention. The initial cognitive function measurement establishes an initial baseline for the subject. The cognitive function can be measured using an established cognitive test such as the delayed verbal recall task of the Wechsler Memory Scale-revised. Thereafter, after treatment the subject is tested again with the delayed verbal recall task of the Wechsler Memory Scale-revised to establish a second measurement. A clinically significant amount is established when the comparison of the second measurement to the first measurement demonstrates an improvement of at least about 1%. Preferably, the improvement in cognitive function, as measured by the delayed verbal recall task of the Wechsler Memory Scale-revised, is between about 1% and 20%. More preferably, the improvement is between about 1% and 10%. Most preferably, the improvement is between about 1% and 5%. It is understood by one skilled in the art that other methods of determining cognitive function improvement are equally applicable as long as they do not measure stages of dementia.

Accordingly, the invention encompasses methods of improving cognitive or neurological function by administering a therapeutically effective amount of at least one active agent that activates P2Y receptors to a subject in need thereof, wherein the improvement in cognitive or neurological function is measured as a score increase between about 1% and 20% in the in the delayed verbal recall task of the Wechsler Memory Scale-revised. The method may further comprise administering at least one phosphatide precursor to the subject.

The method of treatment may encompass administration of the composition as needed to obtain the desired therapeutic effect. The composition can be administered as long as necessary to maintain the desired therapeutic effect. In one embodiment, the composition is administered between about one and 12 months. Preferably, the composition is administered between one and six months. More preferably, the composition is administered between one and three months.

Preferably, the pharmaceutical compositions of the present invention are administered at a dose that produces a desired effect in at least 10% of a population of treated patients. More preferably, the dose is that which produces the effect in at least 20% of treated patients. More preferably, the effect is produced in at least 30% of treated patients. More preferably, the effect is produced in at least 40% of the patients. More preferably, the effect is produced in at least 50% of the patients. More preferably, the effect is produced in at least 60% of the patients. More preferably, the effect is produced in at least 70% of the patients. More preferably, the effect is produced in at least 80% of the patients. Even more preferably, the effect is produced in at least 90% of the patients. Most preferably, the effect is produced in over 90% of the patients.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In one aspect of the invention, the active agent is administered in an amount between about 5 mg/day and 10 g/day. Preferably, each dose of the active agent is in an amount between about 5 mg/dose and 10 g/dose. For example, satisfactory results are obtained by oral administration of the active agents of the invention at dosages between about 0.05 and 10 mg/kg/day, preferably between about 0.1 and 7.5 mg/kg/day, more preferably between about 0.1 and 2 mg/kg/day, most preferably 0.5 mg/kg/day administered once or, in divided doses, 2 to 4 times per day. On administration parenterally, for example by i.v. drip or infusion, dosages between about 0.01 and 5 mg/kg/day, preferably between about 0.05 and 1.0 mg/kg/day and more preferably between about 0.1 and 1.0 mg/kg/day can be used. Suitable daily dosages for patients are thus between about 2.5 and 500 mg p.o., preferably between about 5 and 250 mg p.o., more preferably between about 5 and 100 mg p.o., or between about 0.5 and 250 mg i.v., preferably between about 2.5 and 125 mg i.v. and more preferably between about 2.5 and 50 mg i.v.

For all such treatments described above, the exact formulation, route of administration and dosage can be chosen by the individual physician in view of the patient's condition. (See e.g. Brunton et al., Goodman & Gilman's The Pharmacological Basis of Therapeutics, Eleventh Edition, McGraw-Hill Professional; 2005). It should be noted that the attending physician would know how to and when to terminate, interrupt, or adjust administration due to toxicity or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and the route of administration. The dose and perhaps dose frequency, will also vary according to the age, body weight, and response of the individual patient.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Use of pharmaceutically acceptable carriers to formulate the compositions herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compositions of the invention to be formulated as tablets, pills, capsules, liquids, gels, syrups, slurries, suspensions and the like, for oral ingestion by a patient to be treated.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

A pharmaceutical composition of the present invention for parenteral injection can comprise microparticles or microcapsules in the form of pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include, but are not limited to, water, ethanol, polyols, such as glycerol, propylene glycol, polyethylene glycol, and the like, polymers, vegetable oils and injectable organic esters such as ethyl oleate. The pharmaceutical compositions may further comprise surfactants and adjuvants, such as, but not limited to, preservatives, wetting agents, emulsifying agents, dispersing agents, isotonic agents, antibacterial and antifungal agents.

The active agent may be administered using intravenous infusion, an implantable osmotic pump, a transdermal patch, liposomes, or other modes of administration. In one embodiment, a controlled release system is placed in proximity to the therapeutic target, i.e., the brain, thus requiring only a fraction of the systemic dose.

Solid dosage forms for oral administration include, but are not limited to, capsules, microcapsules, lozenges, dragees, tablets, microtablets, pills, powders, granules and a food base. The ingredients of the compositions of the invention may be mixed with at least one pharmaceutically acceptable excipient or carrier and/or fillers, binders such as, for example, carboxymethylcellulose, alginates, gelatin, polyvinylpyrrolidone, sucrose, acacia, cornstarch, gelatin, carbomer, ethyl cellulose, guar gum, hydroxypropyl cellulose, hydroxypropyl methyl cellulose and povidone, humectants such as glycerol, disintegrating agents, such as cornstarch, potato starch, alginic acid, silicon dioxide, croscarmelose sodium, crospovidone, guar gum and sodium starch glycolate, wetting agents, lubricants such as talc, calcium stearate, magnesium stearate, solid polyethylene glycols, sodium lauryl sulfate, detergents, such as Tween 20, Tween 80, Pluronic F68 and bile acid salts, permeation enhancers, anti-oxidants, such as ascorbic acid, sodium metabisulfite and butylated hydroxyanisole, stabilizers, such as hydroxypropyl cellulose and hyroxypropylmethyl cellulose, viscosity increasing agents, such as carbomer, colloidal silicon dioxide, ethyl cellulose and guar gum, sweeteners, such as aspartame and citric acid, preservatives, such as thimerosal, benzyl alcohol and parabene buffering agents of various pH and ionic strength, and mixtures thereof.

The oral solid dosage forms of the invention may be coated with coatings and shells such as slow-release coatings, sustained-release coatings, controlled-release coatings, enteric coatings and other coatings well known in the pharmaceutical formulating art.

Pharmaceutical preparations for oral use can be obtained by combining the compositions with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Liquid dosage forms for oral administration include, but are not limited to, pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. The oral compositions may also include adjuvants such as wetting agents, emulsifying and suspending agents, sweetening, flavoring, and perfuming agents. Suspensions, in addition to the active compounds, may contain suspending agents such as, for example, ethoxylated isostearyl alcohols, polyoxyethylene sorbitol and sorbitan esters, microcrystalline cellulose, and mixtures thereof.

Also included in the present invention are particulate compositions coated with polymers (e.g. poloxamers or poloxamines) and compositions comprising the active agent of the invention coupled to antibodies directed against tissue-specific receptors, ligands or antigens or coupled to ligands of tissue-specific receptors.

The active compounds in the compositions of the invention may be modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. These modified compounds may exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity is achieved by the administration of such polymer-compound abducts less frequently or in lower doses than with the unmodified compound.

The active agents in the compositions of the invention may be formulated in a neutralized pharmaceutically acceptable salt form. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutical compositions comprising the active agent of the invention may be administered chronically. As used herein, "chronic administration" refers to regular administration. In one embodiment of the invention, chronic administration may be performed indefinitely, e.g., for chronic persistent brain diseases. In other embodiment of the invention, chronic administration is performed for at least one month; at least 6 weeks; at least two months; at least 3 months; at least 4 months; at least 5 months; at least 6 months; at least 9 months; at least one year; at least 1.5 years; at least 2 years; or for more than 2 years. In yet other aspects of the invention, chronic administration is until a follow-up visit or until re-assessment of the disease or disorder being treated.

The pharmaceutical compositions comprising the active agent of the invention may be administered at regular intervals. Administration may be daily, 1-2 times per day, 1-3 times per day, 1-4 times per day, 2-3 times per day, 2-4 times per day, 3-4 times per day, 2-5 times per day, 3-5 times per day, 4-5 times per day, weekly, 1-2 times per week, 1-3 times per week, 2-3 times per week, 1-4 times per week, 1-5 times per week, 2-5 times per week, or 3-5 times per week.

One of ordinary skill will appreciate that effective amounts of the active agents of the invention may be determined empirically and may be employed in pure form or, where such forms exist, in pharmaceutically acceptable salt, ester or pro-drug form. The active agents can be administered to a subject in need of prophylaxis or treatment of a disorder related to synapse deficiency, as pharmaceutical compositions in combination with one or more pharmaceutically acceptable excipient. It will be understood that, when administered to a human subject, the total daily usage of the agents or composition of the present invention will be decided by the attending physician within the scope of sound medical judgment. The specific therapeutically effective dose level for any particular subject will depend upon a variety of factors: the type and degree of the cellular response to be achieved; activity of the specific active agent or composition employed; the specific active agents or composition employed; the age, body weight, general health, sex and diet of the patient; the time of administration, route of administration, and rate of excretion of the active agent; the duration of the treatment; drugs used in combination or coincidental with the specific active agent; and like factors well known in the medical arts. For example, it is well within the skill of the art to start doses of the active agents at levels lower than those required to achieve the desired therapeutic effect and to gradually increase the dosages until the desired effect is achieved.

The dosing can also be arranged in a subject specific manner to provide a predetermined concentration of the agents in the blood, as determined by techniques accepted and routine in the art. Thus, the dosing can be adjusted to achieve regular on-going blood levels, as measured by HPLC, on the order of between about 50 and 1000 ng/ml, preferably between about 150 and 500 ng/ml of the active agent.

The invention also encompasses a method for increasing the level of synaptic proteins in a subject comprising administering a composition having at least one active agent, wherein the protein is NF-70, NF-M, PSD-95, or mGluR. In another embodiment, the method further comprises administering at least one phosphatide precursor to the subject.

The invention also encompasses a method for screening in vitro a drug for enhancing brain synaptogenesis and/or activating brain P2Y receptors comprising incubating neuron-derived cells with the drug and determining the effect of the drug on the level of synaptic proteins and neurites in the cell. In another embodiment, the method further comprises administering at least one phosphatide precursor to the subject.

In one embodiment of this invention, a composition comprising active agent may be used as a dietary or nutritional supplement. In this embodiment, the total daily dose ranges of the active agent and phosphatide precursor for the conditions described herein are generally between about 0.1 mg and about 1000 mg of active agent. A preferred total daily dose is between about 0.5 mg and about 100 mg of the active agent. The composition of this embodiment may further comprise at least one phosphatide precursor. The phosphatide precursor may be present between about 0.1 and 80 mg.

In another embodiment, a total daily dose of the composition may be used as a dietary supplement is between about 0.1 mg and about 1000 mg of active agent. In another embodiment, the composition may further comprise between about 0.1 and 80 mg of phosphatide precursor. The composition may be administered twice daily (e.g., in the morning and the evening). The dosage forms and compositions may comprise any of the forms and compositions described supra. In a preferred embodiment, the formulation comprising active agent and phosphatide precursor is a tablet, capsule, gel, or a liquid-soluble powder.

It will be readily apparent to one of ordinary skill in the relevant art that other suitable modifications and adaptations to the methods and applications described herein can be made without departing from the scope of the invention or any embodiment thereof.

EXAMPLES

Example 1

Screening and Identification of P2Y Receptor Activators

Postsynaptic protein PSD-95 is a member of the membrane-associated guanylate kinase (MAGUK) family. The protein is almost exclusively located in the postsynaptic density of neurons and is involved in anchoring synaptic proteins. The inventor hypothesized that active agents that increase the level of the PSD-95 protein in cultured cells may be screened for their ability to activate P2Y receptors in animal models.

PC12 cells, a cell line ultimately derived from neural cells, are maintained in Minimal Essential Medium (MEM; Invitrogen, Carlsbad, Calif.) supplemented with 10% fetal bovine serum (FBS) at 37° C. Experimental incubations are for 2 or 4 days in medium with or without test compounds.

The activity of each test compound is assessed by determining the effect of each test compound on the level of PSD-95 in the cells. The activity of each test compound is assessed (a) as the sole active ingredient in the medium; (b) in the presence of choline, uridine and DHA; (c) in the presence of choline and DHA.

Test compounds that significantly raise the level of the PSD-95 protein in tissue culture are then tested in laboratory animals for their ability to increase brain dendritic spines. The laboratory animals are fed a food composition with or without a synthetic diet enriched with uridine, DHA and choline for 6 weeks, and are then intraperitoneally injected with a composition comprising the test compound.

Treatment with a pharmaceutical composition comprising any of ADP,ATP disodium salt, BzATP triethylammonium salt, α,β-Methyleneadenosine 5'-triphosphate trisodium salt, 2-Methylthio-ADP trisodium salt, 2-Methylthioadenosine triphosphate tetrasodium salt, 2-MeSATP, MRS 2341, MRS 2365, MRS 2690, MRS 2698, denufosol, PSB 0474, Uridine β-thiodiphosphate (UDPβS), uridine γ-thiophosphate (UTPγS), 2-ThioUTP tetrasodium salt, UTPγS trisodium salt, uridine-5'-diphosphoglucose, uridine 5'-triphosphate (UTP), uridine 5'-diphosphate (UDP), diuridine triphosphate, $Ap_4U$, $Ap_4A$, INS365, INS37217, INS48823, 2-(hexylthio) (HT)-AMP, diadenosine pentaphosphate, 2'-deoxy-2'-amino-UTP, 2-thio-UTP, GTP, ITP, CTP, α,β-methylene ATP, UDP-glucose, suramin analogs, dipyridamole analogs or diadenosine tetraphosphate according to the invention are effective in increasing the level the PSD-95 protein in tissue culture and the level brain dendritic spines in laboratory animals. The effect of each compound is enhanced in the presence of uridine, DHA and choline. These results show that each of the test compounds is effective in increasing the production of synapses in the brain, and the effect is augmented in the presence of phosphatide precursors.

Example 2

In Vivo Administration of the Pharmaceutical Composition of the Invention Increases Levels of NF-70 and NF-M in Brains of Ages Rats In order to assess whether the pharmaceutical compositions of the invention can augment the production of new synaptic membrane in the brain, levels of neurofilament-70 (NF-70) and neurofilament-M (NF-M), which are biomarkers of neurite outgrowth, are assessed in the brains of rats.

Male middle aged rats are obtained from the National Institute on Aging (Harlan Sprague-Dawley, Indianapolis, Ind.). Rats are housed individually under standard husbandry conditions and exposed to 12 hr light/dark cycle with food and water provided ad libitum.

Rats are acclimated to the animal facility for more than 7 days before fed a control laboratory diet (Teklad Global 16% protein rodent diet, TD.00217, Harlan Telclad, Madison, Wis.), or a diet fortified with the pharmaceutical composition of the invention with or without a synthetic diet enriched with uridine, DHA and choline for 6 weeks.

Rats are weighed at the time of beginning feeding (t=0), as well as 1, 2, 4, 6 weeks later. At time 0, rats are randomly assigned into three groups. There are no significant differences of body weight between groups. Experiments are performed twice.

At the end of the 6-week period, the rats are anesthetized with ketamine (85 mg/kg of body weight, intramuscularly) and decapitated in a cold room at 4° C. Brains are rapidly removed and placed into chilled (4° C.) oxygenated Krebs buffer containing 1 mM ketamine and 15 μg/ml eserine. Striatal tissues are placed in Eppendorf tubes containing 200 μl lysis buffer (60 mM Tris-HCl, 4% SDS, 20% glycerol, 1 mM dithiothreitol, 1 mM AEBSF, 8 μM aprotinin, 500 μM bestatin, 15 μM E64, 200μ.M leupeptin, 10 μM pepstatin A). The samples are sonicated, boiled (10 mM), and centrifuged (14,000 g for 1 mM at room temperature) The supernatant fluid is transferred to a clean tube, and total protein content is determined using the Bicinchoninic Acid assay (Sigma, St. Louis, Mo.). Equal amounts of protein (40 μg protein/lane) are loaded on sodium dodecyl sulfate-polyacrylamide gel electrophoresis (4-15% SDS PAGE; Bio-Rad, Hercules, Calif.). Prior to gel electrophoresis, bromphenol blue solution (0.07%) is added to each sample. Proteins are separated, transferred onto polyvinylidene difluoride (PVDF) membranes (Immobilon-P, Millipore), and blocked with 5% bovine serum albumin (Tris-buffered saline/0.15% Tween 20) for 1 h. The proteins are then rinsed in Tris-buffered saline (TBST), and blots are incubated in TBST with various antibodies against the proteins of interest, including NF-70, NF-M (1:2000, 1:5000, respectively; Calbiochem, La Jolla, Calif.) at 4° C. overnight on an orbital shaker. Protein-antibody complexes are detected and visualized using the ECL system (Amersham, Piscataway, N.J.) and Kodak X-AR film, respectively, as suggested by the manufacturer. Films are digitized using a Supervista S-12 scanner with a transparency adapter (UMAX Technologies, Freemont, Calif.). Analysis is performed using the public domain NIH Image program.

Dietary supplementation of the pharmaceutical composition of the invention for 6 weeks significantly increases the levels of NF-70 and NF-M as compared to control values.

Example 3

Administration Increases Neurite Outgrowth, Branching and NF-70 and NF-M Levels in PC-12 Cells Neurite Outgrowth Studies PC12 cells are sparsely plated on collagen-coated 60 mm culture dishes in MEM containing 1% fetal bovine serum. Experimental groups are as follows: pharmaceutical composition of the invention, reactive blue 2, suramin and PPADS (Sigma, St. Louis, Mo.). All treatments are performed 24 h after plating. At the end of the treatment period, images are obtained with a phase-contrast Zeiss Axioplan 2 microscope, using OpenLab software. Six digital images are captured for each dish, for a total of 18 to 24 images per treatment group. Approximately 300 cells are quantified for each treatment group for each experiment. Experiments are performed in triplicate. Quantification of neurites, including neurite branching and neurite length, is performed. Neurite length is measured using the public domain NIH software "Image J." Processes longer than the diameter of the cell body are counted as neurites. Only process-bearing cells are analyzed.

The effect of treatment with the pharmaceutical composition of the invention (10-200 μM) on NGF-induced neurite outgrowth is next tested. In the absence of NGF, PC12 cells do not sprout neurites (fewer than 1%). In the presence of NGF, the pharmaceutical composition of the invention (50-200 μM) significantly ($p<0.01$ or $0.001$) enhances the number of neurites per cell after 4 days of treatment.

The effect of the pharmaceutical composition of the invention on neurite branching and length in the presence of NGF is also assessed. After 4 days of treatment with the pharmaceutical composition of the invention (50 μM) and NGF, the numbers of neurite branch points per cell are significantly increased, compared with those in cells treated with only NGF.

Neurofilament proteins are highly enriched within neurites; therefore, an increase in neurite number should be associated with increased expression of neurofilament proteins. NF-70 (70 kD) and NF-M (145 kD) levels following 4-day treatment of PC 12 cells with NGF alone, or NGF plus the pharmaceutical composition of the invention (50 μM) are thus measured. Both NF-70 and NF-M expression significantly increases following treatment, compared to cells treated only with NGF. Thus, treatment with the pharmaceutical composition of the invention augments neurite outgrowth in PC 12 cells.

In conclusion, the pharmaceutical composition of the invention increases the levels of two major neurofilament proteins in rat brain, and is directly shown to induce neurite outgrowth in PC 12 cells.

Example 4

NGF-Differentiated PC 12 Cells Express Pyrimidine-Sensitive P2Y2, P2Y4, P2Y6 and P2Y14 Receptors Detection of P2Y Receptors Western blots utilized rabbit anti-P2Y2, anti-P2Y4 (both from Calbiochem); or rabbit anti-P2Y6 (Novus Biologicals, Littleton, Colo.).

PC 12 cells treated as described above are grown on 12 mm glass cover slips (A Daigger & Co., Vernon Hills, Ill.) coated with collagen. Proteins are visualized using immunofluorescence. Briefly, the cells are fixed with 4% paraformaldehyde, permeabilized with 0.25% Triton X-100, blocked in 10% normal goat serum, and incubated overnight in the presence of the appropriate antibodies (mouse anti-NF-70, and either rabbit anti-P2Y2, rabbit anti-P2Y4 or rabbit anti-P2Y6). For P2Y2 and P2Y4 visualization, control cultures are incubated with primary antibody plus a control antigen in order to ensure that the immuno-staining is specific. Cells are then incubated in fluorochrome-conjugated secondary antibodies for 1 hour (goat anti-rabbit ALEXA 488 and goat anti-mouse ALEXA 568; Molecular Probes, Eugene, Oreg.) and mounted on glass slides with mounting media with or without DAPI (Vector Laboratories, Burlingame, Calif.). Control antigens provided with the primary antibodies are used to ensure that immuno-staining is specific. Digital images are then obtained.

UTP is an agonist of the pyrimidine-activated class of P2Y receptors, namely P2Y2, P2Y4 and P2Y6 receptors. To determine whether these receptors participate in the mechanism by which extracellular UTP affects neurite outgrowth, it is first determined whether the receptors are expressed in PC12 cells, and whether exposure to NGF alters their expression. PC 12 cells are treated for 0-7 days with NGF and levels of the receptors measured. After 3 days of NGF treatment, expression of the P2Y2 receptor reaches maximal levels, which are significantly higher than those seen at less than 3 days of NGF treatment. To visualize the expression and localization of the P2Y2, as well as the P2Y4 and P2Y6 receptors, cells are grown in the presence or absence of NGF for 4 days and then immuno-stained with the neuritic marker NF-70. All three receptors are highly expressed in NGF-differentiated PC12 cells. In addition, P2Y2 co-localizes with the neuronal marker MAP-2. Thus, the P2Y2, P2Y4 and P2Y6 receptors are present in neural cells, but not in their precursors.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for improving cognitive or neurological function in a subject in need thereof comprising administering a therapeutically effective amount of an active agent that activates P2Y receptors and a phosphatide precursor to the subject, wherein the active agent is uridine diphosphate and the phosphatide precursor comprises at least one omega-3 fatty acid, thereby the cognitive or neurological function is improved by increasing outgrowth of a brain cell which expresses P2Y receptors.

2. The method according to claim 1, wherein the improvement in cognitive function is measured as a score increase between 1% and 10% in the delayed verbal recall task of the Wechsler Memory Scale-revised.

3. The method according to claim 1, wherein the improvement in cognitive function is measured as a score increase between 1% and 20% in the delayed verbal recall task of the Wechsler Memory Scale-revised.

4. The method according to claim 1, wherein the phosphatide precursor further comprises glucose, or choline.

5. The method according to claim 1, wherein the omega-3 fatty acid is DHA or EPA.

6. The method according to claim 1, wherein the active agent is present in an amount between about 0.1 mg and 500 mg.

7. The method according to claim 1, wherein the active agent is present in an amount between about 0.5 mg and 100 mg.

8. The method according to claim 1, wherein the improvement in cognitive function is measured as a score increase between 1% and 5% in the delayed verbal recall task of the Wechsler Memory Scale-revised.

9. The method according to claim 1, wherein the subject suffers from a neurogenerative disease selected from the group consisting of Alzheimer's disease, Parkinson's Disease, Huntington's Disease, Prion Disease, and Amyotrophic lateral sclerosis.

10. The method according to claim 1, wherein the subject has suffered a concussion, a stroke, partial or total spinal cord transection, brain injury, or malnutrition.

11. The method according to claim 1, wherein the subject has suffered toxic neuropathies, meningoencephalopathies, or a vascular disease.

12. The method according to claim 1, wherein the composition is administered orally, nasally, parenterally, systemically, intraperitoneally or topically.

* * * * *